(12) United States Patent
Lee et al.

(10) Patent No.: US 12,409,410 B1
(45) Date of Patent: Sep. 9, 2025

(54) REFRIGERATOR TO REDUCE THE DETERIORATION RATE OF STORED ITEMS USING PLASMA AND PHOTOCATALYST

(71) Applicants: Sang Dae Lee, Suwon-si (KR); Sim Won Yuk, Jeonju-si (KR)

(72) Inventors: Sang Dae Lee, Suwon-si (KR); Sim Won Yuk, Jeonju-si (KR)

( * ) Notice: Subject to any disclaimer, the term of this patent is extended or adjusted under 35 U.S.C. 154(b) by 0 days.

(21) Appl. No.: 19/022,458

(22) Filed: Jan. 15, 2025

(30) Foreign Application Priority Data

Nov. 24, 2023 (KR) .................. 10-2023-0165780

(51) Int. Cl.
*B01D 53/32* (2006.01)
*A23B 2/00* (2025.01)
(Continued)

(52) U.S. Cl.
CPC .............. *B01D 53/32* (2013.01); *A23B 2/003* (2025.01); *A23B 2/708* (2025.01); *A61L 9/205* (2013.01); *A61L 9/22* (2013.01); *B01D 53/007* (2013.01); *B01D 53/72* (2013.01); *B01J 21/063* (2013.01); *B01J 35/39* (2024.01); *F24F 8/30* (2021.01); *H05H 1/471* (2021.05);
(Continued)

(58) Field of Classification Search
CPC .............. F25D 17/042; F25D 2317/00; F25D 2317/04; F25D 2317/041; H01T 19/04; H01T 23/00
USPC .................................................... 422/186.04
See application file for complete search history.

(56) References Cited

U.S. PATENT DOCUMENTS

| | | | |
|---|---|---|---|
| 2008/0047433 A1 | 2/2008 | Ouyang et al. | |
| 2011/0271702 A1* | 11/2011 | Miyashita | A23B 4/015 62/264 |

(Continued)

FOREIGN PATENT DOCUMENTS

| | | | | |
|---|---|---|---|---|
| CN | 205580088 U | 9/2016 | | |
| FR | 2839262 A1 * | 11/2003 | ............... | A61L 9/22 |

(Continued)

OTHER PUBLICATIONS

Korean Office Action of No. 10-2023-0165780 dated Mar. 25, 2024.
Korean Notice of Decision to Grant a Patent of No. 10-2023-0165780 dated Jul. 19, 2024.

*Primary Examiner* — James Lin
*Assistant Examiner* — John Lee
(74) *Attorney, Agent, or Firm* — Sughrue Mion, PLLC

(57) ABSTRACT

The present invention relates to a refrigerator designed to reduce the deterioration rate of stored items, such as food, fruits, vegetables, meat, flowers, and plants, within the storage compartment using plasma and a photocatalyst. Specifically, the invention performs filtering with a photocatalyst and plasma sterilization on the air in the storage compartment to decompose ethylene gas and other substances, thereby reducing the deterioration rate of stored items and extending their storage period. The invention utilizes a compact high-density plasma generator with discharge electrodes and ground electrodes arranged in multiple cells. Plasma is uniformly and multidimensionally generated in the air within the storage compartment, decomposing ethylene gas to slow the deterioration rate of food, fruits, vegetables, meat, flowers, and plants, and extending their storage period.

7 Claims, 10 Drawing Sheets

(51) Int. Cl.
    *A23B 2/708*     (2025.01)
    *A61L 9/20*     (2006.01)
    *A61L 9/22*     (2006.01)
    *B01D 53/00*     (2006.01)
    *B01D 53/72*     (2006.01)
    *B01J 21/06*     (2006.01)
    *B01J 35/39*     (2024.01)
    *F24F 8/30*     (2021.01)
    *H05H 1/24*     (2006.01)

(52) U.S. Cl.
    CPC ........ *A61L 2209/11* (2013.01); *A61L 2209/12* (2013.01); *A61L 2209/14* (2013.01); *B01D 2255/20707* (2013.01); *B01D 2255/802* (2013.01); *B01D 2257/7022* (2013.01); *B01D 2257/708* (2013.01); *B01D 2257/91* (2013.01); *B01D 2259/804* (2013.01); *B01D 2259/818* (2013.01); *H05H 2245/15* (2021.05)

(56) References Cited

U.S. PATENT DOCUMENTS

| | | | |
|---|---|---|---|
| 2018/0272024 A1* | 9/2018 | Seo | A61L 9/205 |
| 2022/0331816 A1 | 10/2022 | Park et al. | |
| 2023/0093679 A1* | 3/2023 | Son | H01T 23/00 |
| | | | 361/220 |

FOREIGN PATENT DOCUMENTS

| | | | | |
|---|---|---|---|---|
| JP | 2007-289832 A | | 11/2007 | |
| JP | 2011-115569 A | | 6/2011 | |
| JP | 2017013041 A | * | 1/2017 | ........... A47L 9/1683 |
| JP | 2017-123990 A | | 7/2017 | |
| KR | 10-2004-0034636 A | | 4/2004 | |
| KR | 10-1065361 B1 | | 9/2011 | |
| KR | 10-2111772 B1 | | 5/2020 | |
| KR | 10-2221407 B1 | | 3/2021 | |
| KR | 10-2021-0054719 A | | 5/2021 | |
| KR | 10-2022-0052199 A | | 4/2022 | |
| KR | 10-2023-0077245 A | | 6/2023 | |

* cited by examiner

REFRIGERATOR TO REDUCE THE DETERIORATION RATE OF STORED ITEMS USING PLASMA AND PHOTOCATALYST

CROSS-REFERENCE TO RELATED APPLICATION

This application claims priority to and the benefit of Korean Patent Application No. 10-2023-0165780, filed on Nov. 24, 2023, the disclosure of which is incorporated herein by reference in its entirety.

BACKGROUND

1. Field of the Invention

The present invention relates to a refrigerator configured to reduce the deterioration rate of stored items such as food, fruits, vegetables, meat, flowers, and plants within a storage compartment over time using plasma and a photocatalyst. Specifically, the invention pertains to a refrigerator that performs filtering using a photocatalyst and plasma sterilization on the air within the storage compartment, thereby decomposing ethylene gas and other substances in the air to reduce the deterioration rate of stored items, such as food, fruits, vegetables, meat, flowers, and plants, and extend their storage period.

2. Discussion of Related Art

To store temperature-sensitive products such as refrigerated or frozen foods and vaccines in a refrigerated or frozen state, refrigerators equipped with an insulated storage compartment and a cooling device to lower the temperature inside the compartment are commonly used. These refrigerators maintain the storage compartment below a specific temperature by circulating air through a heat exchanger corresponding to the condenser of the refrigeration system, and a blower fan adjacent to the heat exchanger. A refrigerator is a device that keeps the temperature of stored items, such as food, fruits, vegetables, meat, flowers, and plants, at a low temperature to maintain their freshness and quality.

However, items stored in a refrigerator, including food, fruits, vegetables, meat, flowers, and plants, often spoil or wilt quickly due to exposure to ethylene gas ($C_2H_4$) that naturally occurs in the air, making long-term storage difficult. Ethylene gas is a plant hormone naturally emitted by fruits and vegetables. It plays a crucial role in regulating processes such as growth, development, and ripening in plants. During the ripening process of fruits, the production of ethylene gas increases significantly. As ethylene gas accelerates the ripening of fruits and vegetables, its precise management is critical during storage. Uncontrolled ethylene gas can hasten food spoilage or cause underripe produce to ripen prematurely. Since fruits and vegetables continue to emit ethylene gas during storage, the surrounding environment in the storage compartment inevitably contains ethylene gas. Therefore, managing ethylene gas levels and ensuring proper storage conditions are essential during food storage. If fruits and vegetables are stored alongside other items, such as meat, in the refrigerator's storage compartment, the ethylene gas emitted by the produce can affect the environment surrounding the meat, potentially impacting the freshness of other foods. Consequently, when storing meat with fruits or vegetables, careful attention must be given to managing the effects of ethylene gas.

To address this issue, methods for decomposing ethylene gas using plasma generators have been proposed. A plasma generator is a device that induces partial discharge by applying a high voltage, ranging from several kV to thousands of kV, between positive and negative electrodes. Plasma generators are typically incorporated into electronic devices such as air purifiers or air conditioners. For instance, an air purifier disperses positive and negative ions generated by an internal plasma generator into the air to purify indoor spaces. Similarly, an air conditioner equipped with a plasma generator cools the air while simultaneously purifying the indoor space by dispersing positive and negative ions.

When a piezoelectric transformer amplifies and outputs voltage, and the high voltage is applied to the needle electrodes, plasma is generated in the surrounding space of the electrodes. According to conventional technology, using a plasma generator with a pair of needle electrodes to sterilize large spaces required multiple plasma generators. However, increasing the number of plasma generators to maintain sterilization capacity proportionally increased ozone production, which was problematic. Additionally, in conventional designs, the needle electrodes of small plasma generators attached to the airflow path were smaller than the overall airflow area, resulting in limited active volume for sterilization. This inefficiency reduced sterilization effectiveness since only part of the air was sterilized.

Thus, there is a need for a refrigerator that can utilize compact high-density plasma generators to generate plasma multidimensionally within the storage compartment, effectively decomposing ethylene gas to reduce the deterioration rate of stored items, such as food, fruits, vegetables, meat, flowers, and plants, and extending their storage period.

Photocatalyst filters are effective for decomposing ethylene gas. These filters use photocatalytic processes to break down pollutants into harmless substances. The core component of a photocatalyst filter is a photocatalytic material, such as titanium dioxide ($TiO_2$). When exposed to UV or specific wavelengths of visible light, the photocatalyst is activated, generating reactive oxygen species. These reactive species interact with pollutants, such as ethylene gas, in the air, breaking them down. Activated photocatalysts decompose ethylene gas into carbon dioxide and water. The carbon dioxide and water produced are released into the air, reducing the effects of ethylene gas pollution. Photocatalyst filters do not produce chemical additives or byproducts, making them an environmentally friendly solution for removing ethylene gas. Additionally, photocatalyst filters operate effectively for extended periods without requiring regular replacement or replenishment, as they do not degrade or rely on chemical inputs. Photocatalyst filters are effective at decomposing a variety of airborne pollutants, including low concentrations of gases such as ethylene. This makes them particularly useful for reducing ethylene gas levels in the storage compartments of refrigerators used to store food, agricultural products, or meat.

Therefore, there is a need for a refrigerator that uses compact high-density plasma generators and photocatalyst filters to remove ethylene gas, reducing the deterioration rate of stored items such as food, fruits, vegetables, meat, flowers, and plants within the storage compartment, and extending their storage period.

SUMMARY OF THE INVENTION

The present invention aims to achieve the following objectives to address the problems described above.

The present invention is directed to providing a refrigerator that reduces the deterioration rate of stored items, such as fresh products including food, fruits, vegetables, meat, flowers, and plants, within the storage compartment.

The present invention is further directed to providing a refrigerator that performs filtering and plasma sterilization on the air within the storage compartment to decompose ethylene gas and other substances, thereby reducing the deterioration rate of stored items, such as food, fruits, vegetables, meat, flowers, and plants, and extending their storage period.

The present invention is also directed to providing a refrigerator that utilizes a compact high-density plasma generator, in which plasma is uniformly and multidimensionally generated using discharge electrodes and ground electrodes included in multiple cells. By generating plasma multidimensionally within the storage compartment, the refrigerator decomposes ethylene gas to slow down the deterioration rate of stored items, such as food, fruits, vegetables, meat, flowers, and plants, and extends their storage period.

The present invention is further directed to providing a refrigerator that uses a photocatalyst filter to reduce the concentration of ethylene gas within the storage compartment, thereby slowing the deterioration rate of fresh products, such as food, fruits, vegetables, meat, flowers, and plants, and extending their storage period during storage.

The objectives of the present invention are not limited to those mentioned above, and other unmentioned objectives should be clearly understood by those of ordinary skill in the art based on the following description.

Various embodiments of the present invention provide a refrigerator for reducing a deterioration rate of stored items using plasma and a photocatalyst filter. The refrigerator includes a storage compartment for storing and retrieving at least one of food, fruits, vegetables, meat, flowers, or plants; an openable and closable door; a cooling device for cooling air within the storage compartment; and an air purification device for purifying air within the storage compartment. The air purification device includes: a photocatalyst filter for removing particles in the air within the storage compartment; a plasma generator for performing plasma sterilization on the air within the storage compartment; a ventilation fan configured to direct air passing through the photocatalyst filter to the plasma generator and discharge the air into the storage compartment; a high-voltage generator comprising a battery and configured to generate a high voltage for generating plasma within the plasma generator from a voltage output from the battery; and a controller comprising at least one processor. The photocatalyst filter includes: a filter medium coated with titanium dioxide ($TiO_2$), which is a photocatalytic material; and a lamp configured to emit visible light or ultraviolet light to the photocatalyst material. The plasma generator includes: a plurality of discharge needle electrodes arranged in cells on an XY plane, wherein peaks of the cells are oriented in a Z-axis direction at centers of the cells; ground electrodes formed on the XY plane at a same height as the peaks and arranged around the cells to correspond one-to-one with the peaks; a guide block on which the ground electrodes are installed on an upper portion, and having grooves into which the plurality of discharge needle electrodes are inserted; a first terminal electrically connected to the plurality of discharge needle electrodes and a second terminal electrically connected to the ground electrodes. The ground electrodes are configured as ground pads made of a conductive material, with electrode holes in circular or polygonal shapes arranged in m rows and n columns, sharing a common center with the peaks of the plurality of discharge needle electrodes. The guide block is configured in a cylindrical shape with a common center aligned with the peaks of the plurality of discharge needle electrodes, and includes a tunnel arranged corresponding to the cells. The guide block is further configured such that a first diameter of the tunnel is largest at a bottom and gradually decreases toward the ground electrodes along a direction of an airflow.

BRIEF DESCRIPTION OF THE DRAWINGS

The above and other objects, features, and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, exemplary embodiments of the present invention will be described in detail with reference to the accompanying drawings to allow those of ordinary skill in the art to which the present invention pertains to easily practice the present invention. The present invention may be implemented in various different forms and is not limited to the embodiments described herein.

Figure 1:
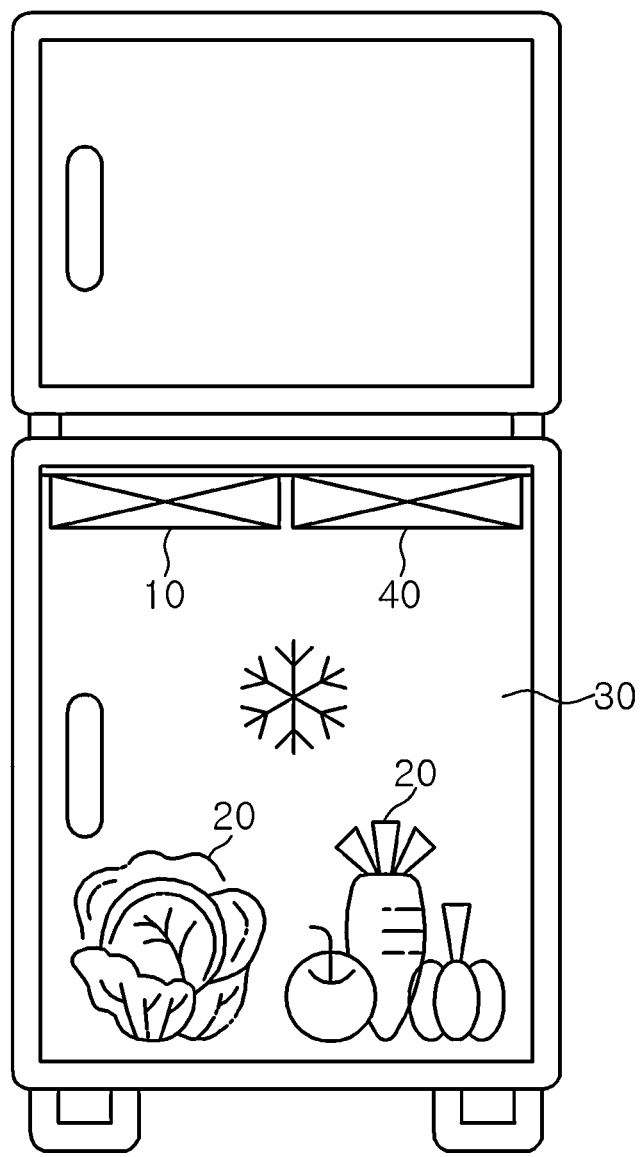
FIG. 1 illustrates an example of a refrigerator according to an embodiment of the present invention.

FIG. 1 illustrates an example of a refrigerator according to an embodiment of the present invention.

Refrigerator 1 stores perishable items 20, such as food, fruits, vegetables, meat, flowers, and plants, in a storage compartment 30 as time passes. Refrigerator 1 includes a storage compartment 30 for placing and retrieving stored items 20, an openable and closable door (not shown), an air purification device 10, and a cooling device 40. Refrigerator 1, according to an embodiment of the present invention, comprises a cooling device 40 for cooling air within storage compartment 30 and an air purification device 10 for purifying air within storage compartment 30 (i.e., air inside refrigerator 1).

The present invention relates to refrigerator 1, which includes a cooling device 40 and an air purification device 10, to reduce the deterioration rate and extend the storage period of stored items 20, such as food, fruits, vegetables, meat, flowers, and plants, within storage compartment 30. Specifically, the present invention pertains to refrigerator 1, which performs photocatalytic filtering and plasma sterilization on the air in storage compartment 30 to decompose ethylene gas and other substances. This process lowers the deterioration rate and extends the storage period of stored items 20, such as food, fruits, vegetables, meat, flowers, and plants, within storage compartment 30.

Figure 2:
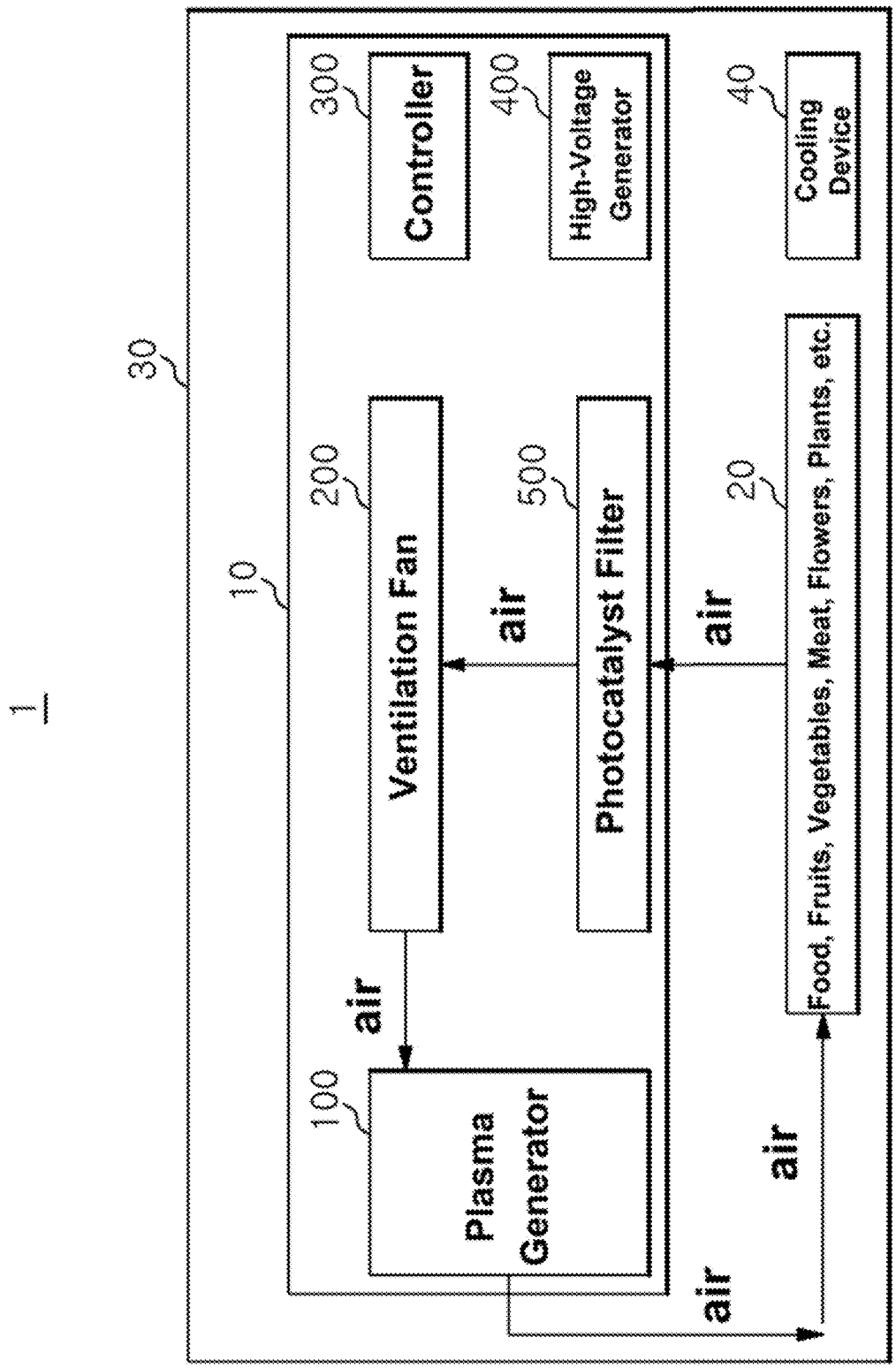
FIG. 2 illustrates an example of the configuration of a refrigerator according to an embodiment of the present invention.

FIG. 2 illustrates an example of the configuration of a refrigerator according to an embodiment of the present invention.

Referring to FIG. 2, refrigerator 1 includes a storage compartment 30 for placing and retrieving stored items 20, a cooling device 40 for cooling air within storage compartment 30, and an air purification device 10 for purifying air within storage compartment 30. Refrigerator 1 may further include an openable and closable door (not shown). Cooling device 40 may be configured as a conventional air conditioning system.

Refrigerator 1 can accommodate stored items 20, such as food, fruits, vegetables, meat, flowers, and plants, within storage compartment 30.

Air purification device 10 includes a plasma generator 100, a ventilation fan 200, a controller 300, a high-voltage generator 400, and a photocatalyst filter 500. These components are electrically interconnected.

Plasma generator 100 operates by receiving a boosted voltage from high-voltage generator 400, which applies high voltage to positive and negative electrodes to generate optical plasma. Plasma generator 100 is powered by a direct current voltage supplied by high-voltage generator 400. For generating optical plasma, plasma generator 100 emits multi-wavelength light in the range of vacuum ultraviolet (VUV) wavelengths (100 nm) to general sterilization ultraviolet (UV-A) wavelengths (400 nm). The optical plasma generated by plasma generator 100 can destroy organic molecular contaminants in the air. Vacuum ultraviolet wavelengths provide sufficient photon energy for optical plasma generation. Light wavelengths in the 100-280 nm range not only break molecular (M) bonds due to the activation of electrons (e) in organic compounds but also initiate oxygen plasma generation at room temperature. Optical plasma, in its highly energized state, produces reactive cleaning agents such as excited-state electrons (e), ionized air, and hydroxyl radicals (OH·). These reactive cleaning agents generated by optical plasma can break down organic pollutants such as ethylene gas ($C_2H_4$).

The ventilation fan 200 is configured to draw air from inside the storage compartment 30, directing the air that has passed through the photocatalyst filter 500 toward the plasma generator 100. The ventilation fan 200 blows air onto the positive and negative electrodes of the plasma generator 100, allowing the optical plasma generated by the plasma generator 100 to diffuse throughout the storage compartment 30.

The controller 300 controls the overall operation of the air purification device 10 and may consist of at least one processor.

The high-voltage generator 400 may include a battery and boosts the voltage of the power supplied by the battery to output high voltage. The voltage of the power supplied by the battery may range from 3.5V to 12V, depending on the battery's charge state. The high-voltage output from the high-voltage generator 400 may be approximately 5000V. The high-voltage generator 400 can be configured using a direct current (DC)-DC converter. One technology that may be used for this is the Cockcroft-Walton Voltage Multiplier or another type of voltage multiplier. This method amplifies direct current (DC) voltage using a series of voltage doublers or a diode-capacitor structure. In this structure, the voltage is doubled at each stage, and by connecting multiple stages, the desired voltage can be achieved. The high voltage generated by the high-voltage generator 400 is supplied to the plasma generator 100.

The photocatalyst filter 500 is configured to filter harmful substances, such as fine dust, from the air inside the storage compartment 30. The air that has passed through the photocatalyst filter 500 is introduced into the plasma generator 100 by the ventilation fan 200.

The photocatalyst filter 500 may include a filter medium coated with titanium dioxide ($TiO_2$) as the photocatalyst material and a lamp configured to irradiate visible light or ultraviolet light onto the photocatalyst material.

Figure 3:
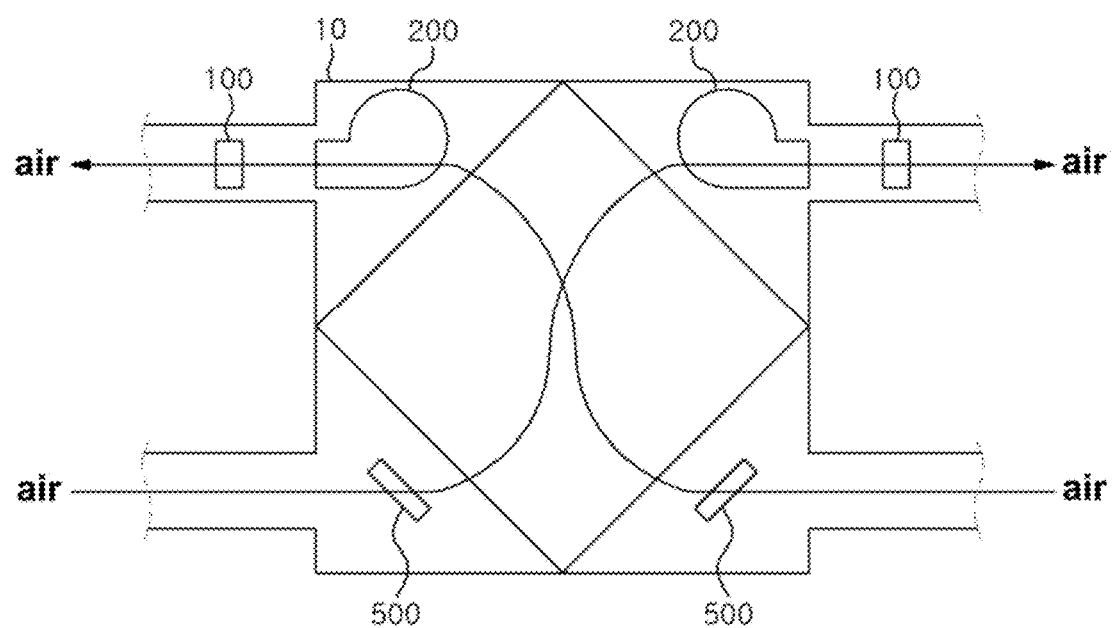
FIG. 3 illustrates an example of the configuration of an air purification device including a photocatalyst filter and a plasma generator in a refrigerator according to an embodiment of the present invention.

FIG. 3 illustrates an example of the configuration of an air purification device, including a photocatalyst filter and a plasma generator, within a refrigerator according to an embodiment of the present invention.

Referring to FIG. 3, the air purification device 10 is configured to direct air passing through the photocatalyst filter 500 into the plasma generator 100 and discharge it using the ventilation fan 200.

Air entering the air purification device 10 is filtered as it passes through the photocatalyst filter 500, and organic substances, such as ethylene gas ($C_2H_4$), contained in the air are destroyed by the optical plasma generated by the plasma generator 100. Consequently, the quality of air supplied into the storage compartment 30 is improved, slowing the deterioration rate and extending the storage period of stored items such as food, fruits, vegetables, meat, flowers, and plants.

Furthermore, air passing through the plasma generator 100 is discharged into the storage compartment 30 using the ventilation fan 200.

The configuration shown in FIG. 3 is exemplary, and the arrangement of the photocatalyst filter 500, ventilation fan 200, and plasma generator 100 within the air purification device 10 may vary from the example depicted in FIG. 3.

Figure 4:
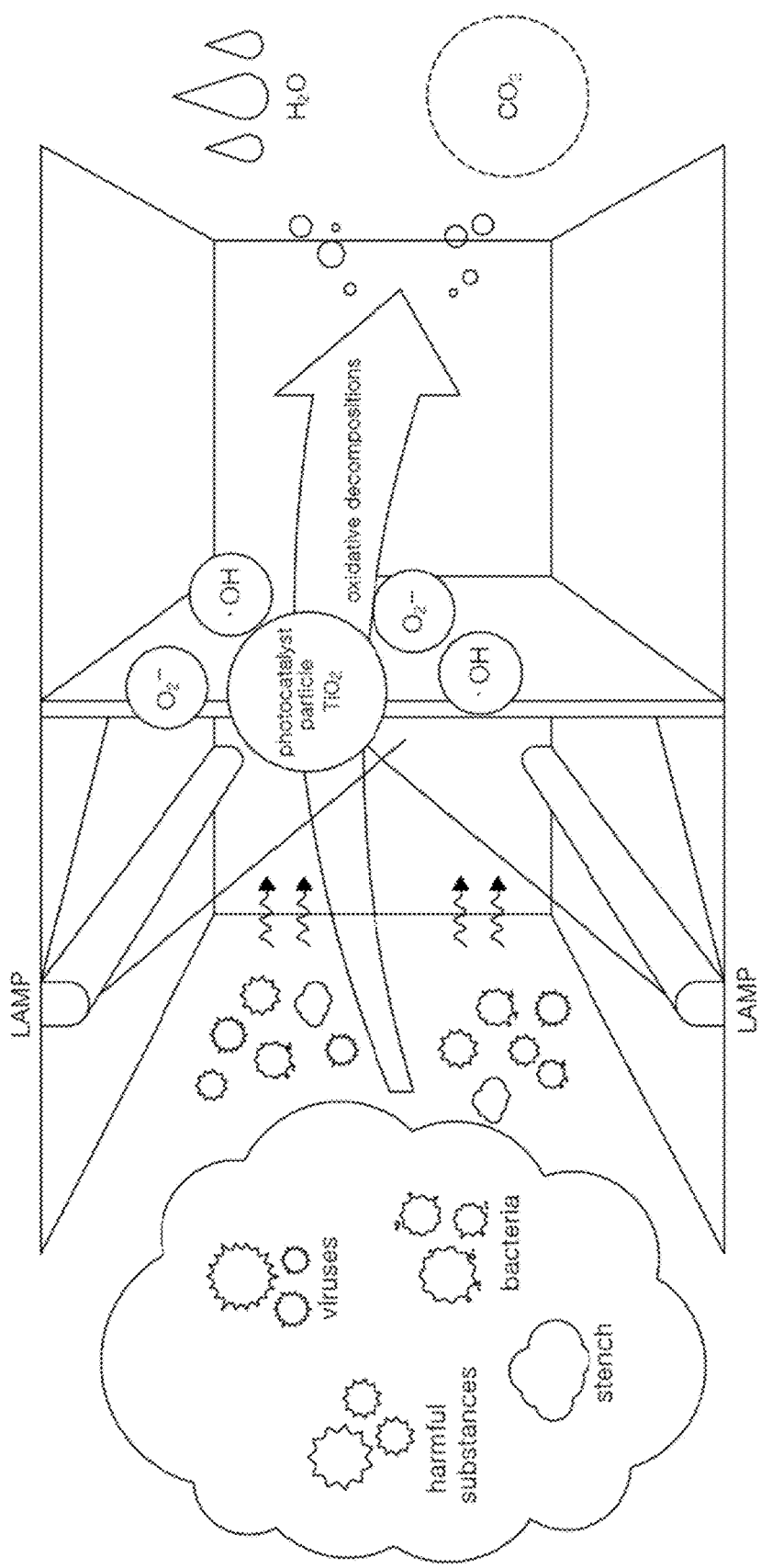
FIG. 4 illustrates an example of the configuration of a photocatalyst filter in a refrigerator according to an embodiment of the present invention.

FIG. 4 illustrates an example of the configuration of a photocatalyst filter within a refrigerator according to an embodiment of the present invention.

The photocatalyst filter is a device that decomposes and removes pollutants using a photocatalytic reaction. Such filters are commonly used in air purification and water treatment applications, with titanium dioxide ($TiO_2$) being a widely used photocatalyst material.

The photocatalyst filter depicted in FIG. 4 includes a filter medium coated with titanium dioxide ($TiO_2$), which is the photocatalyst material, and a lamp configured to irradiate visible or ultraviolet light to induce photocatalytic reactions on the photocatalyst material. The filter medium coated with titanium dioxide ($TiO_2$) may be composed of ceramic, metal, or polymer.

The photocatalyst filter can decompose or remove harmful substances, odors, bacteria, and viruses. The lamp or light source in the photocatalyst filter is often a UV lamp, but visible light lamps, such as visible light LEDs, may also be used. When exposed to light from the photocatalyst filter, the titanium dioxide ($TiO_2$) is activated as a photocatalyst particle, promoting the photocatalytic reaction. Through this reaction, reactive oxygen species such as superoxide anion radicals ($O_2^-$) and hydroxyl radicals (OH·) are generated. Superoxide anion radicals ($O_2^-$) are one type of reactive oxygen species produced during the photocatalytic reaction and play a critical role in decomposing harmful substances. Hydroxyl radicals (OH·) are another highly reactive oxygen species generated during the photocatalytic reaction, effectively breaking down harmful substances. The photocatalytic reaction oxidatively decomposes harmful substances into harmless compounds. For example, volatile organic compounds (VOCs) and other harmful chemicals can be decomposed into $CO_2$ and $H_2O$. When harmful substances are decomposed by the photocatalytic reaction, they are converted into water ($H_2O$) and carbon dioxide ($CO_2$), both of which are harmless to humans. VOCs refer to organic compounds that evaporate or volatilize easily at room temperature under atmospheric pressure. VOCs are emitted from various sources, with ethylene ($C_2H_4$) being one example. Ethylene is a naturally released VOC during plant growth and ripening processes and is also industrially utilized, where it may be released as a VOC during these applications.

The operation of the photocatalyst filter involves light activation, oxidation of pollutants, and the generation of water and carbon dioxide. During light activation, the photocatalyst material is activated by UV light, generating electrons and holes. During the oxidation of pollutants, these electrons and holes react with pollutants in the air, such as VOCs, microorganisms, and viruses, oxidizing them. During the generation of water and carbon dioxide, the oxidized pollutants are primarily decomposed into water and carbon dioxide. Ethylene ($C_2H_4$) is also decomposed into water and carbon dioxide through reactions with the electrons and holes generated by the activated photocatalyst material.

The photocatalytic reaction of the photocatalyst filter can effectively eliminate microorganisms such as viruses, bacteria, and fungi. Additionally, the filter can decompose harmful chemicals like VOCs into harmless water and carbon dioxide. The photocatalyst filter is particularly effective at decomposing and removing substances that cause spoilage in food and other items.

Figure 5:
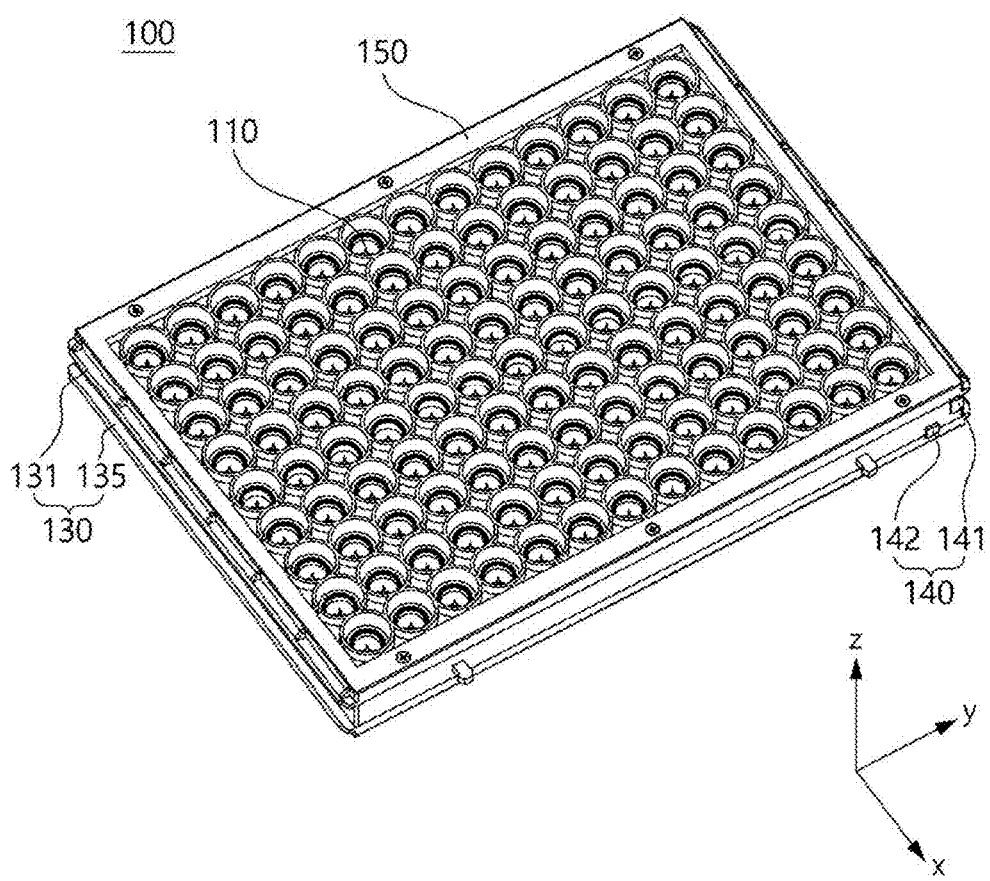
FIG. 5 illustrates a perspective view of a plasma generator in a refrigerator according to an embodiment of the present invention.

FIG. 5 illustrates a perspective view of a plasma generator within a refrigerator according to an embodiment of the present invention.

Referring to FIG. 5, the plasma generator 100 may be configured to include a plurality of cells arranged in multiple rows (m) and columns (n), for example, 13 rows and 9 columns as shown in FIG. 5, to generate large-area plasma.

Although the cross-sectional shape of the cells in FIG. 5 is depicted as circular, it is not limited to this shape and may include at least one shape selected from circles, ellipses, and polygons. Similarly, as shown in FIG. 5, the stacked blocks 130, 150 and the holes 151, 121, 132, 136 formed in the ground electrode 120 may also have at least one shape selected from circles, ellipses, and polygons, similar to the cells.

Figure 6:
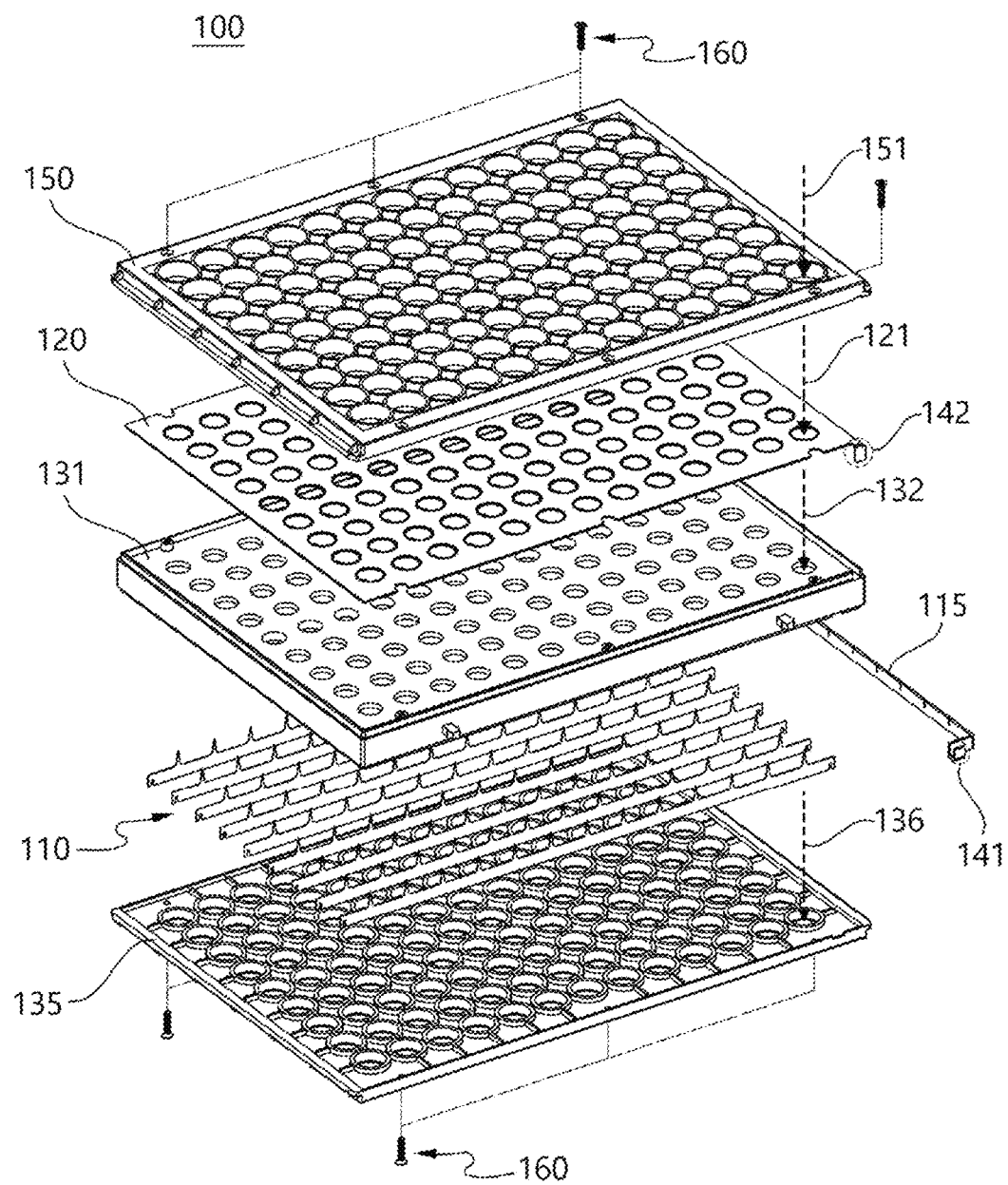
FIG. 6 illustrates an exploded perspective view of a plasma generator in a refrigerator according to an embodiment of the present invention.

FIG. 6 illustrates an exploded perspective view of a plasma generator within a refrigerator according to an embodiment of the present invention.

Referring to FIG. 6, the holes formed in the upper block 150 are referred to as exhaust ports 151, the holes formed in the ground electrode 120 as electrode holes 121, the holes formed in the upper guide block 131 as tunnels 132, and the holes formed in the bottom block 135 as inlet passages 136.

As shown in FIGS. 5 and 6, the plasma generator 100 may be configured to include discharge needle electrodes 110, a ground electrode 120, a guide block 130, terminals 140, and an upper block 150. The ground electrode 120, guide block 130, and upper block 150 may be joined using coupling means 150, such as screws.

The discharge needle electrodes 110 may be arranged in a plurality of cells on the XY plane, with the peak 111a of each electrode positioned at the center of each cell and oriented in the Z-axis direction. Additionally, the plurality of discharge needle electrodes 110 may be arranged such that the peaks are oriented in the direction of airflow. Specifically, the discharge needle electrodes 110 may have needle-shaped peaks positioned at the center of each cell and directed downstream of the airflow. This arrangement is designed to minimize airflow resistance. If air does not circulate smoothly, for instance, if air stagnates around the discharge needle electrodes 110, the likelihood of ozone generation may increase.

The plurality of discharge needle electrodes 110 may be electrically connected to the high-voltage generator 400 via the first terminal 141. The method for connecting the plurality of discharge needle electrodes 110 will be described later.

The ground electrode 120 may have a ground pad shape made of a conductive material, with electrode holes 121 formed in a circular or polygonal shape and arranged in multiple rows (m) and columns (n) aligned with the peaks of the discharge needle electrodes 110. Referring again to FIG. 6, the plurality of ground electrodes 120 may be implemented as a single connected ground pad. When the electrode holes 121 are formed on a plate-shaped conductor aligned in rows and columns, the ground electrode 120 can be completed. The plurality of electrode holes 121 may include at least one shape selected from circles or polygons.

The ground electrode 120 may be formed on the XY plane at the same height as the peak of the discharge needle electrode 110 and arranged around the cell in a one-to-one correspondence with the peak. The height of the ground electrode 120 will be described later.

The guide block 130 serves to secure the discharge needle electrodes 110 and the ground electrode 120. Specifically, the ground electrode 120 may be seated on the upper portion of the guide block 130, and the plurality of discharge needle electrodes 110 may be inserted into grooves formed in the guide block 130. The plurality of discharge needle electrodes 110 may be fixed into the grooves of the guide block 130 either individually or grouped together. The shape of the discharge needle electrodes 110 will be described later.

Referring to FIG. 6, the guide block 130 may have a cylindrical shape with a common center aligned with the peak of the discharge needle electrodes 110 and may include tunnels 132 arranged to correspond to the cells. The tunnels 132 will be described later.

The guide block 130 may consist of one piece or two pieces, depending on the direction in which the discharge needle electrodes 110 are inserted. For example, if the discharge needle electrodes 110 are inserted into grooves formed on the upper portion of the guide block 130, the guide block 130 may consist of a single piece. In this case, the upper portion of the guide block 130 may be covered by the upper block 150. If the grooves for inserting the discharge needle electrodes 110 are formed on the lower portion of the guide block 130, a bottom block 135 will be required to cover the lower portion.

In other words, the guide block 130 may be configured to include an upper guide block 131 positioned below the ground electrode 120 and a bottom block 135 positioned below the upper guide block 131. The tunnels formed in the bottom block 135 correspond to the inlet passage 136, where air flows in from upstream of the airflow.

Referring to FIG. 6, terminal 140 may be configured to include a first terminal 141 electrically connected to the plurality of discharge needle electrodes 110 and a second terminal 142 electrically connected to the ground electrode 120. It is preferable for terminal 140 to be formed as a single pair, as shown in FIG. 6, rather than being individually formed for each electrode. Therefore, a medium to facilitate electrical connections between the electrodes and the terminal may be present.

Referring to FIG. 6, the plasma generator 100 may be configured to include a top block 150 that secures the ground electrode 120 on the upper portion of the guide block 130. The ground electrode 120 may be positioned between the top block 150 and the upper guide block 131.

The top block 150 may be configured to include an exhaust passage 151 connected to the tunnel 132 downstream of the airflow. The diameter of the exhaust passage 151 may gradually increase in the direction of the airflow. The details of the diameter of the exhaust passage 151 will be described later.

Figure 7:
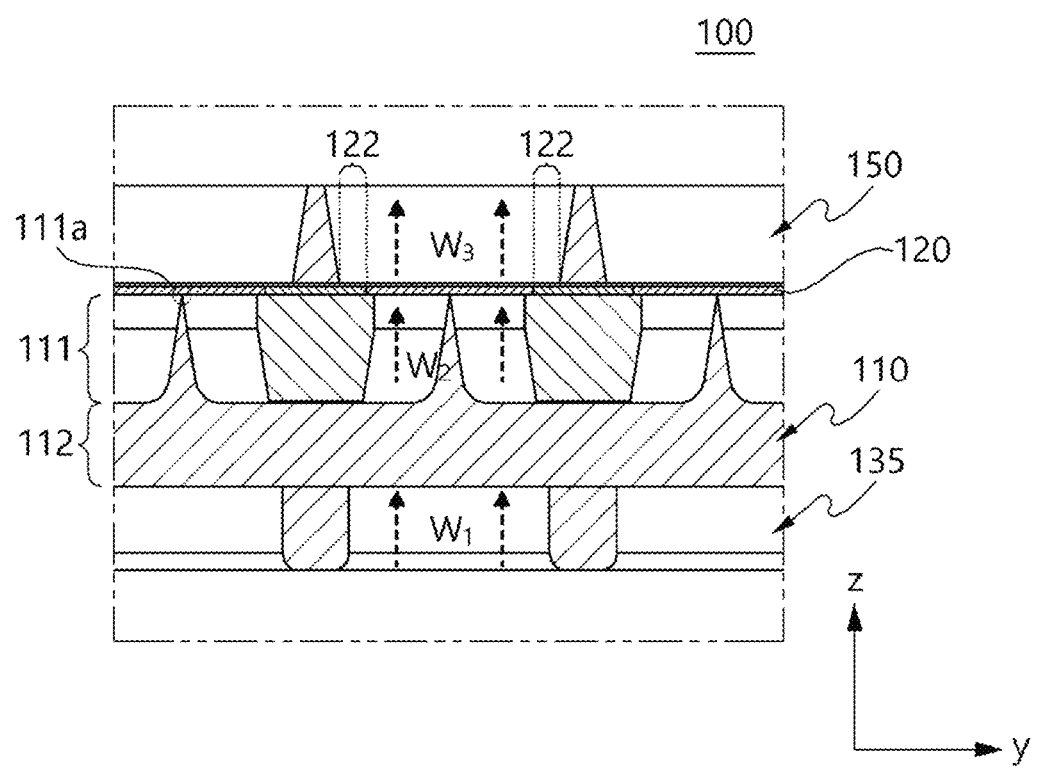
FIG. 7 illustrates an example of a cross-sectional view parallel to the y-axis of a plasma generator in a refrigerator according to an embodiment of the present invention.

FIG. 7 illustrates an example of a cross-section parallel to the y-axis of the plasma generator in a refrigerator according to an embodiment of the present invention. Referring to FIG. 7, the longitudinal cross-section of the plasma generator 100, formed by bisecting the discharge needle electrodes 111, is depicted. The plurality of discharge needle electrodes 110 may be configured to include individual discharge needle electrodes 111 and electrode connectors 112.

Figure 8:
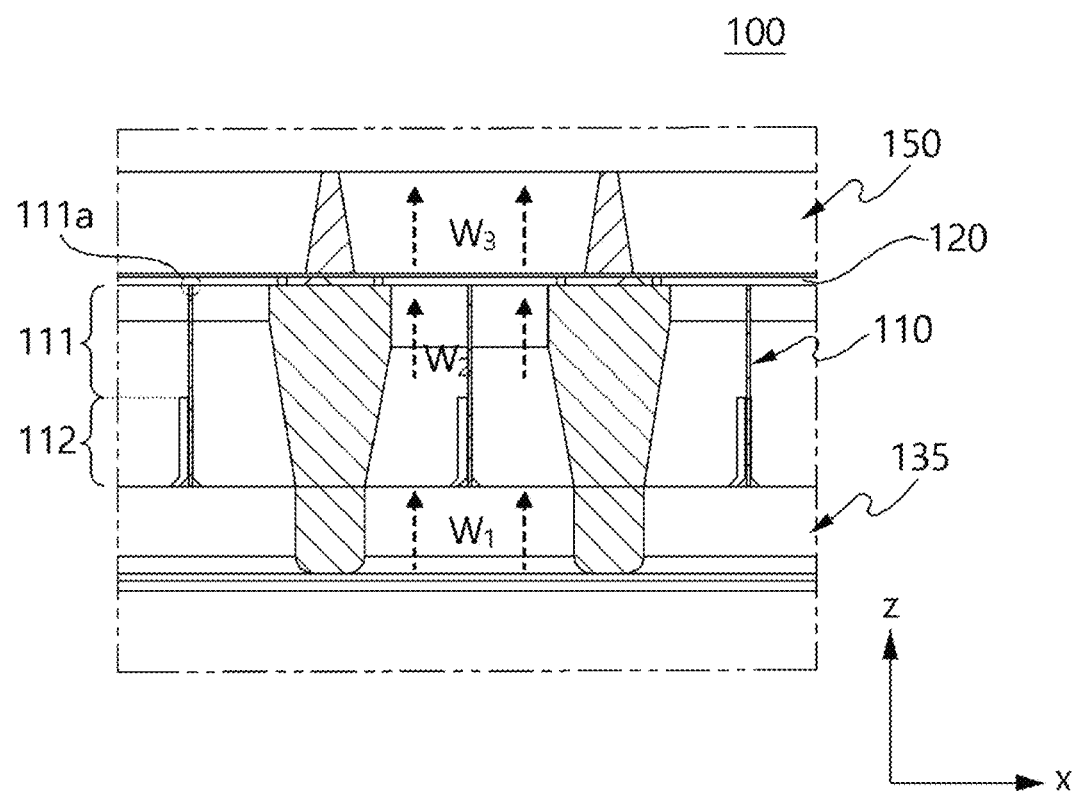
FIG. 8 illustrates an example of a cross-sectional view parallel to the x-axis of a plasma generator in a refrigerator according to an embodiment of the present invention.

FIG. 8 illustrates an example of a cross-section parallel to the x-axis of the plasma generator in a refrigerator according to an embodiment of the present invention.

Referring to FIG. 8, the cross-section of the plasma generator 100 in the width direction, formed by bisecting the peak 111a of the discharge needle electrodes 111, is depicted. W1, W2, and W3 represent the airflow.

Referring to FIGS. 7 and 8, W1, W2, and W3 indicate the airflow. Along the Z-axis direction, the top block 150 is positioned at the top, with the ground electrode 120 placed in contact with the top block 150. Below the ground electrode 120, the upper guide block 131 and the bottom block 135 are sequentially arranged.

W1 represents the airflow in the inlet passage 136, W2 represents the airflow in the tunnel 132, and W3 represents the airflow in the exhaust passage 151.

The guide block 130 may be configured such that the diameter of the tunnel 132 is largest at the bottom and gradually decreases toward the ground electrode 120 along the direction of the airflow. According to Bernoulli's principle, the velocity of a fluid is inversely proportional to the cross-sectional area. Therefore, as the diameter of the tunnel 132 narrows along the direction of airflow, the velocity of the airflow within the tunnel 132 increases, enabling smooth air discharge.

Referring to FIGS. 7 and 8, the ground electrode 120 may be formed on the XY plane at the same height as the peak 111a of the discharge needle electrodes 110, arranged around the cells in a one-to-one correspondence with the peak 111a. In other words, the electrode holes 121 formed in the ground electrode 120 may be positioned at the same height as the peak 111a of the discharge needle electrodes 110. The peak 111a of the discharge needle electrodes 111 may thus be located between the upper and lower surfaces of the pad forming the ground electrode 120. The position and shape of the discharge needle electrodes 111 and the ground electrode 120 are related to plasma parameters.

Figure 9:
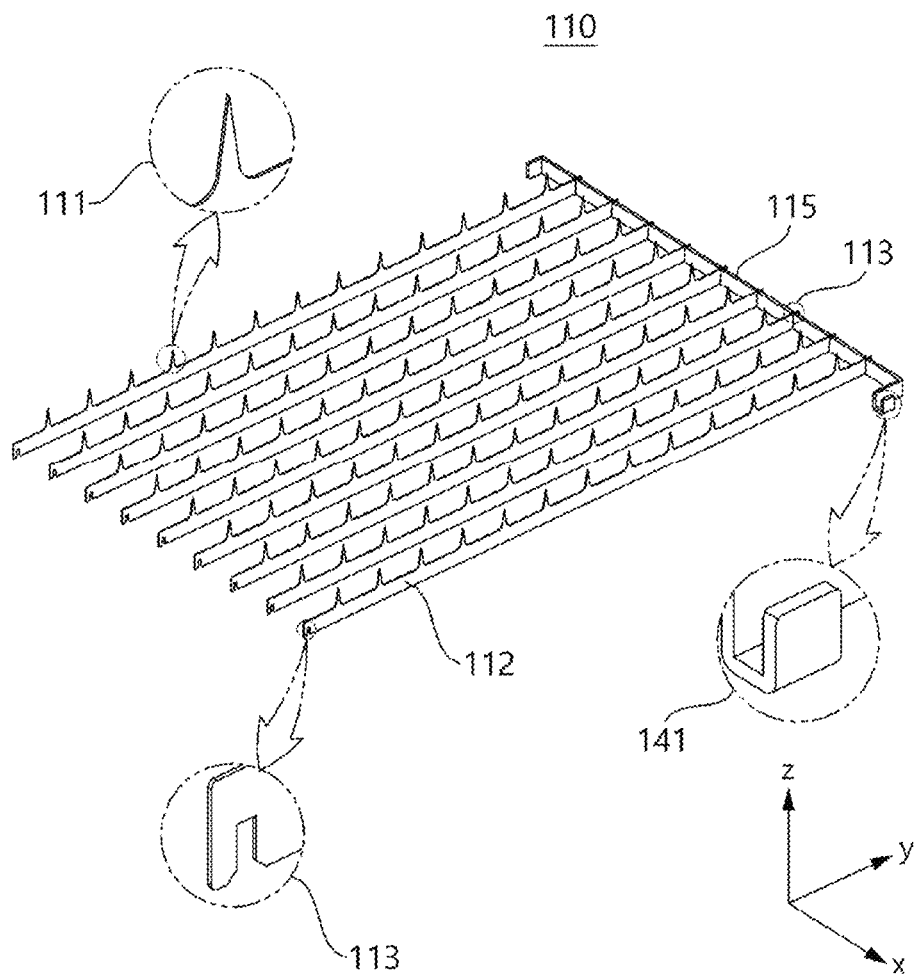
FIG. 9 illustrates an example of a plurality of discharge needle electrodes of a plasma generator in a refrigerator according to an embodiment of the present invention.

FIG. 9 illustrates an example of a plurality of discharge needle electrodes in a plasma generator within a refrigerator according to an embodiment of the present invention.

Referring to FIG. 9, the plurality of discharge needle electrodes 110 may include discharge needle electrodes 111 in rows (m) or columns (n) of the cell arrangement, and are configured to further include a plurality of electrode connectors 112 electrically connecting the individual discharge needle electrodes 111 in rows (m) or columns (n), and cross connectors 115 electrically interconnecting the plurality of electrode connectors 112.

The electrode connectors 112 may include fitting grooves 113 formed at one end and the other end. One of the fitting grooves 113 may be configured to accommodate the cross connector 115. These fitting grooves 113 may be provided at both ends for ease of assembly during manufacturing.

The first terminal 141 may be configured to electrically connect to the cross connector 115, and the second terminal 142 may be configured to electrically connect to the ground electrode 120.

Figure 10:
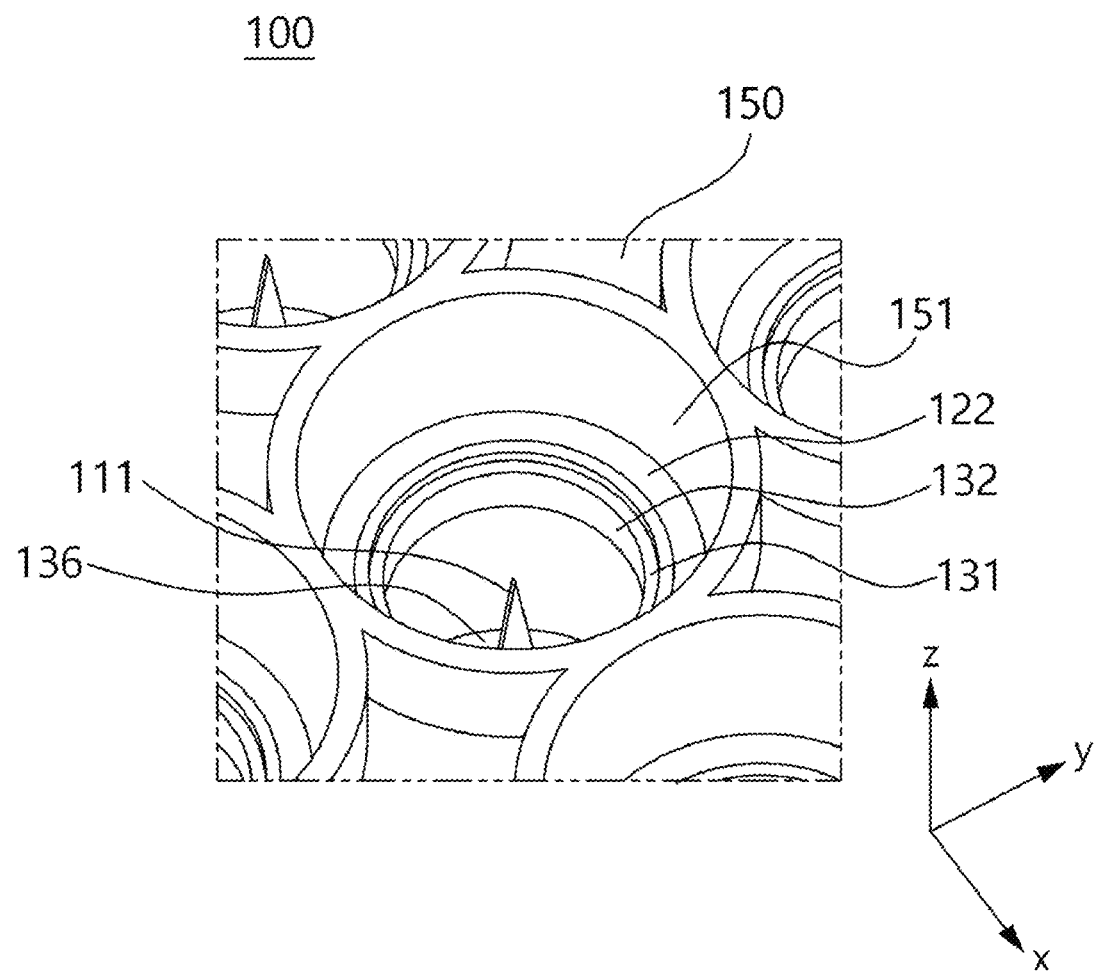
FIG. 10 illustrates an example of a hole edge on a ground electrode of a plasma generator in a refrigerator according to an embodiment of the present invention.

FIG. 10 illustrates an example of the hole edge of the ground electrode in a plasma generator within a refrigerator according to an embodiment of the present invention.

Referring to FIG. 10, the top block 150 may be configured such that the hole edge 122 of the ground electrode 120 in contact with the electrode hole 121 is exposed along a line of sight parallel to the Z-axis. To achieve this, the diameter of the exhaust passage 151 at the height of the ground electrode 120 may be larger than the diameter of the electrode hole 121. Specifically, the hole edge 122 of the ground electrode 120 is exposed between the vertical wall surfaces of the exhaust passage 151 formed by the upper guide block 131 and the top block 150. More precisely, the horizontal hole edge 122 and the vertical wall corresponding to the thickness of the ground electrode 120 are exposed to the air, and these areas are related to discharge in association with individual discharge needle electrodes 111.

As described above, according to one embodiment of the present invention, plasma can be uniformly and multidimensionally generated using the discharge electrodes and ground electrodes included in the plurality of cells. Additionally, smooth airflow reduces the probability of ozone generation. Furthermore, modularized electrodes improve the ease of manufacturing processes for the plasma generator.

According to various embodiments of the present invention, a refrigerator for reducing a deterioration rate of stored items using plasma and a photocatalyst filter is provided. The refrigerator includes a storage compartment for storing and retrieving at least one of food, fruits, vegetables, meat, flowers, or plants; an openable and closable door; a cooling device for cooling air within the storage compartment; and an air purification device for purifying air within the storage compartment. The air purification device includes: a photocatalyst filter for removing particles in the air within the storage compartment; a plasma generator for performing plasma sterilization on the air within the storage compartment; a ventilation fan configured to direct air passing through the photocatalyst filter to the plasma generator and discharge the air into the storage compartment; a high-voltage generator comprising a battery and configured to generate a high voltage for generating plasma within the plasma generator from a voltage output from the battery; and a controller comprising at least one processor. The photocatalyst filter includes: a filter medium coated with titanium dioxide (TiO2), which is a photocatalytic material; and a lamp configured to emit visible light or ultraviolet light to the photocatalyst material. The plasma generator includes: a plurality of discharge needle electrodes arranged in cells on an XY plane, wherein peaks of the cells are oriented in a Z-axis direction at centers of the cells; ground electrodes formed on the XY plane at a same height as the peaks and arranged around the cells to correspond one-to-one with the peaks; a guide block on which the ground electrodes are installed on an upper portion, and having grooves into which the plurality of discharge needle electrodes are inserted; a first terminal electrically connected to the plurality of discharge needle electrodes and a second terminal electrically connected to the ground electrodes. The ground electrodes are configured as ground pads made of a conductive material, with electrode holes in circular or polygonal shapes arranged in m rows and n columns, sharing a common center with the peaks of the plurality of discharge needle electrodes. The guide block is configured in a cylindrical shape with a common center aligned with the peaks of the plurality of discharge needle electrodes, and includes a tunnel arranged corresponding to the cells. The guide block is further configured such that a first diameter of the tunnel is largest at a bottom and gradually decreases toward the ground electrodes along a direction of an airflow.

According to various embodiments of the present invention, the plurality of discharge needle electrodes are arranged such that the peaks are oriented in the direction of the airflow.

According to various embodiments of the present invention, the plurality of discharge needle electrodes further include: a plurality of electrode connectors configured to electrically connect the plurality of discharge needle electrodes in m rows and n columns within arrangements of the cells; and a cross connector configured to electrically interconnect the plurality of electrode connectors. The first terminal is configured to electrically connect to the cross connector.

According to various embodiments of the present invention, the electrode connector includes fitting grooves formed at one end and the other end, and is configured such that one of the fitting grooves accommodates the cross connector.

According to various embodiments of the present invention, the plasma generator further includes: a top block configured to secure the ground electrodes on an upper portion of the guide block. The top block includes: an exhaust passage connected to the tunnel in a downstream of the airflow, the exhaust passage being formed with a second diameter that gradually increases along the direction of the airflow. The top block is configured such that: the second diameter of the exhaust passage at a height of the ground electrodes is larger than a third diameter of the electrode holes, exposing a hole edge area of the ground electrodes in contact with the electrode holes along a line of sight parallel to a Z-axis.

According to various embodiments of the present invention, the filter medium is composed of one of ceramic, metal, or polymer.

According to various embodiments of the present invention, electrons in the titanium dioxide are activated by ultraviolet light emitted from the lamp, and particles in the air are decomposed or neutralized through oxidation and hydroxyl radical formation reactions that occur as the activated electrons interact with hydrogen and oxygen molecules in the air near the filter medium.

The embodiments described above are those in which components and features of the present invention are combined in a predetermined form. Each component or feature should be considered optional unless explicitly stated otherwise. Each component or feature may be implemented in a form that is not combined with other components or features. In addition, it is also possible to constitute an embodiment of the present invention by combining some components and/or features. The order of operations described in the embodiments of the present invention may be changed. Some configurations or features of one embodiment may be included in other embodiments, or may be replaced with corresponding configurations or features of other embodiments. It is obvious that the embodiments may be configured by combining claims that do not have an explicit citation relationship in the claims or may be included as new claims by amendment after filing.

It will be apparent to those skilled in the art to which the present invention pertains that the present invention may be embodied in different forms without departing from the technical spirit and essential features of the present invention. The above embodiments are therefore to be construed in all aspects as illustrative and not restrictive. The scope of rights of the present invention should be determined by rational interpretation of the appended claims and all modifications possible within an equivalent scope of the present invention.

What is claimed is:

1. A refrigerator for reducing a deterioration rate of stored items using plasma and a photocatalyst filter, the refrigerator comprising:
    a storage compartment for storing and retrieving at least one of food, fruits, vegetables, meat, flowers, or plants;
    an openable and closable door;
    a cooling device for cooling air within the storage compartment; and
    an air purification device for purifying air within the storage compartment,
    wherein the air purification device includes: a photocatalyst filter for removing particles in the air within the storage compartment; a plasma generator for performing plasma sterilization on the air within the storage compartment; a ventilation fan configured to direct air passing through the photocatalyst filter to the plasma generator and discharge the air into the storage compartment; a high-voltage generator comprising a battery and configured to generate a high voltage for generating plasma within the plasma generator from a voltage output from the battery; and a controller comprising at least one processor,
    wherein the photocatalyst filter includes: a filter medium coated with titanium dioxide ($TiO_2$), which is a photocatalytic material; and a lamp configured to emit visible light or ultraviolet light to the photocatalyst material,
    wherein the plasma generator includes: a plurality of discharge needle electrodes arranged in cells on an XY plane, wherein peaks of the cells are oriented in a Z-axis direction at centers of the cells; ground electrodes formed on the XY plane at a same height as the peaks and arranged around the cells to correspond one-to-one with the peaks; a guide block on which the ground electrodes are installed on an upper portion, and having grooves into which the plurality of discharge needle electrodes are inserted; a first terminal electrically connected to the plurality of discharge needle electrodes and a second terminal electrically connected to the ground electrodes, wherein the ground electrodes are configured as ground pads made of a conductive material, with electrode holes in circular or polygonal shapes arranged in m rows and n columns, sharing a common center with the peaks of the plurality of discharge needle electrodes, wherein the guide block is configured in a cylindrical shape with a common center aligned with the peaks of the plurality of discharge needle electrodes, and includes a tunnel arranged corresponding to the cells, and wherein the guide block is further configured such that a first diameter of the tunnel is largest at a bottom and gradually decreases toward the ground electrodes along a direction of an airflow.

2. The refrigerator of claim 1, wherein the plurality of discharge needle electrodes are arranged such that the peaks are oriented in the direction of the airflow.

3. The refrigerator of claim 2, wherein the plurality of discharge needle electrodes further include: a plurality of electrode connectors configured to electrically connect the plurality of discharge needle electrodes in m rows and n columns within arrangements of the cells; and a cross connector configured to electrically interconnect the plurality of electrode connectors, wherein the first terminal is configured to electrically connect to the cross connector.

4. The refrigerator of claim 3, wherein the electrode connector includes fitting grooves formed at one end and the other end, and is configured such that one of the fitting grooves accommodates the cross connector.

5. The refrigerator of claim 1, wherein the plasma generator further includes: a top block configured to secure the ground electrodes on an upper portion of the guide block, wherein the top block includes: an exhaust passage connected to the tunnel in a downstream of the airflow, the exhaust passage being formed with a second diameter that gradually increases along the direction of the airflow, and wherein the top block is configured such that: the second diameter of the exhaust passage at a height of the ground electrodes is larger than a third diameter of the electrode holes, exposing a hole edge area of the ground electrodes in contact with the electrode holes along a line of sight parallel to a Z-axis.

6. The refrigerator of claim 1, wherein the filter medium is composed of one of ceramic, metal, or polymer.

7. The refrigerator of claim 1, wherein electrons in the titanium dioxide are activated by ultraviolet light emitted from the lamp, and particles in the air are decomposed or neutralized through oxidation and hydroxyl radical formation reactions that occur as the activated electrons interact with hydrogen and oxygen molecules in the air near the filter medium.

* * * * *